(12) United States Patent
Gonzalez

(10) Patent No.: US 11,678,969 B2
(45) Date of Patent: Jun. 20, 2023

(54) MAGNETIC VASCULAR ACCESS GRAFT

(71) Applicant: Henry Gonzalez, Upland, CA (US)

(72) Inventor: Henry Gonzalez, Upland, CA (US)

( * ) Notice: Subject to any disclaimer, the term of this patent is extended or adjusted under 35 U.S.C. 154(b) by 943 days.

(21) Appl. No.: 16/448,314

(22) Filed: Jun. 21, 2019

(65) Prior Publication Data

US 2020/0375720 A1      Dec. 3, 2020

Related U.S. Application Data

(63) Continuation of application No. 16/430,331, filed on Jun. 3, 2019, now Pat. No. 10,667,898.

(51) Int. Cl.
*A61F 2/06* (2013.01)
*A61L 27/50* (2006.01)
*A61M 1/36* (2006.01)

(52) U.S. Cl.
CPC .............. *A61F 2/06* (2013.01); *A61L 27/507* (2013.01); *A61M 1/3653* (2013.01); *A61F 2002/061* (2013.01); *A61F 2002/068* (2013.01)

(58) Field of Classification Search
CPC .. A61F 2/06; A61M 1/3653; A61M 2205/057
See application file for complete search history.

(56) References Cited

U.S. PATENT DOCUMENTS

| | | | |
|---|---|---|---|
| 4,619,641 A | 10/1986 | Schanzer | |
| 5,454,943 A | 10/1995 | Ashton | |
| 6,261,257 B1 * | 7/2001 | Uflacker | ............. A61M 1/3655 604/175 |
| 6,585,763 B1 | 7/2003 | Keilman | |
| 6,652,540 B1 | 11/2003 | Cole | |
| 7,588,551 B2 | 9/2009 | Gertner | |
| 8,197,683 B2 | 6/2012 | Lopes | |
| 8,652,284 B2 | 2/2014 | Bogert | |
| 9,873,000 B2 | 1/2018 | Moss | |
| 10,144,652 B2 | 12/2018 | Lee | |
| 2008/0277352 A1 | 11/2008 | White | |
| 2010/0318175 A1 | 12/2010 | Abarca | |
| 2011/0264104 A1 | 10/2011 | Naoum | |
| 2014/0336682 A1 | 11/2014 | Naoum | |
| 2016/0331511 A1 | 11/2016 | Kassab | |
| 2018/0289883 A1 | 10/2018 | Gage | |

* cited by examiner

*Primary Examiner* — Leslie R Deak
(74) *Attorney, Agent, or Firm* — Jafari Law Group, Inc.

(57) ABSTRACT

The invention relates to generally to a vascular access graft that includes a magnetic element disposed about a flow tube for guiding a blood flow between an arterial end adapted for arterial anastomosis to a portion of an artery, and a venous end adapted for venous anastomosis to a portion of a vein. The magnetic element may include a plurality of magnets disposed about the flow tube so that a magnetic field may be applied to blood flowing therein; the magnetic element may alternatively include a circuitry configured to generate a magnetic field applied to the flow tube.

18 Claims, 12 Drawing Sheets

MAGNETIC VASCULAR ACCESS GRAFT

PRIORITY NOTICE

The present application is a continuation of U.S. patent application Ser. No. 16/430,331, filed Jun. 3, 2019, the disclosure of which is incorporated herein by reference in its entirety.

TECHNICAL FIELD OF THE INVENTION

The present disclosure relates generally to vascular access grafts, and more specifically to vascular access grafts that implement a magnetic housing configured to apply a magnetic field along a length of the graft in order to disrupt and minimize blood coagulation so as to prolong the life of the graft.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever. Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Vascular access grafts are well known in the art. These devices typically provide an efficient means of introducing or removing chemicals from the bloodstream. For example, in hemodialysis, vascular access grafts are used to remove the patient's blood so that it can be filtered through a dialyzer. In other cases, diseased portions of vasculature are replaced with or supplemented via grafts to facilitate blood flow or to reduce risk of rupture of an aneurysm. The grafts may comprise natural materials, e.g., a portion of a blood vessel taken from another area of the patient's body, or they may comprise artificial materials.

In order to achieve their intended function, prior art vascular access grafts have implemented mechanical, electrical, and even magnetic components. For example, U.S. Pat. No. 6,652,540 to Cole et al. discloses methods for forming magnetic vascular anastomoses, that include devices employing a magnetic force to form a magnetic port in a hollow body. Similarly, U.S. Patent Application Publication 2018/0289883A1 to Gage et al. discloses an apparatus and method for cannulation of vascular access grafts. In that disclosure, a device is taught to include a port that comprises a magnetic component around a cannulation chamber, which facilitates the localization of the port to an operator such as physician or medical personnel. Still other disclosures, such as U.S. Patent Application Publication 2016/0331511A1 to Kassab et al., teach magnetic closures mechanisms that may comprise an arrow-lock configuration, magnetic strips, a series of perforations and sutures and or a series of clips to seal together that device.

However, none of the prior art adequately addresses the issue of prolonging the life of a vascular access graft, particularly by disrupting and minimizing blood coagulation of a blood flowing through the graft. That is, because of the nature of prior art vascular access grafts, they are prone to build-up and often become restricted. Restricted grafts of course mean the velocity and or volume of blood flow through the graft is negatively impacted. As the lumen through a graft gradually becomes occluded with fatty buildup, other deposits or intima, the pressure differential across the graft increases, the velocity of blood in the lumen decreases and the flow of blood through the lumen decreases. To remedy faulty or restricted grafts, these prior art devices are generally designed so that regular (i.e. annual) replacement is expected. Accordingly, it would be beneficial to prolong the life of these devices by minimizing replacement intervals.

Therefore, there is a need for a system and method for a vascular access graft, which addresses the above-mentioned concerns. It is to these ends that the present invention has been developed.

SUMMARY OF THE INVENTION

To minimize the limitations in the prior art, and to minimize other limitations that will be apparent upon reading and understanding the present specification, the present invention describes a system and method for enclosing a vascular access graft in a magnetic housing configured to generate a magnetic field applied to the graft in order to disrupt and minimize blood coagulation so as to prolong the life of the graft.

Generally, the invention involves a vascular access graft that includes a magnetic element disposed about a flow tube for guiding a blood flow between an arterial end adapted for arterial anastomosis to a portion of an artery, and a venous end adapted for venous anastomosis to a portion of a vein. The magnetic element may include a plurality of magnets disposed about the flow tube so that a magnetic field may be applied to blood flowing therein; the magnetic element may alternatively include a circuitry configured to generate a magnetic field applied to the flow tube; in some embodiments, the magnetic element may include a single magnet disposed about the flow tube so that a magnetic field may be applied to blood flowing therein; and in some embodiments, the magnetic element may include a combination of both a circuitry configured to generate a magnetic field applied to the flow tube and one or more magnets disposed about the flow tube so that a magnetic field may be applied to blood flowing therein. It is propositioned that the magnetic field or fields applied to the flow tube generally disrupt atoms that make up the molecules that make up the coagulation proteins, and ultimately, affect the protein function of said coagulation proteins to minimize build-up within the flow tube. More specifically, it is propositioned that the magnetic field or fields applied to the flow tube generally disrupt electron or atomic nuclear net forces, or electron spins, that ultimately affect the coagulation process such that coagulation is avoided within the flow tube housed and enclosed by the magnetic element.

As may be appreciated by those skilled in the art, a system and device in accordance with the present invention may be utilized not only for vascular access grafts, but also for other procedures involving redirecting blood flow from one area to another by reconnecting blood vessels via a flow tube.

A magnetic vascular access device, in accordance with some exemplary embodiments of the present invention, may include: a tubular body of biocompatible material including an arterial end adapted for arterial anastomosis to a portion of an artery, and a venous end adapted for venous anastomosis to a portion of a vein; a housing running through the tubular and adapted to house a flow tube for guiding a blood flow between the arterial end and the venous end; a cavity formed within the housing and adapted to encapsulate the flow tube, the cavity including a magnetic element configured to apply a magnetic field to the blood flow guided through the flow tube; and at least one cannulation port arranged on a surface of the tubular body, the cannulation port configured for receiving needle punctures providing needle access to an interior of the flow tube.

A magnetic vascular access device, in accordance with some exemplary embodiments of the present invention, may include: a tubular body including an arterial end adapted for arterial anastomosis to a portion of an artery, and a venous end adapted for venous anastomosis to a portion of a vein; a flow tube running through the tubular body for guiding a blood flow between the arterial end and a venous end; a housing encapsulating the flow tube and forming a cavity between an exterior of the flow tube and an interior surface of the housing, the cavity including a magnetic element configured to generate a magnetic field applied to the blood flow guided through the flow tube; and at least one port arranged on a surface of the tubular body, the port configured for providing needle access to the flow tube.

A magnetic vascular access device, in accordance with some exemplary embodiments of the present invention, may include: a tubular body of biocompatible material including an arterial end adapted for arterial anastomosis to a portion of an artery, and a venous end adapted for venous anastomosis to a portion of a vein; a first housing running through the tubular body for guiding a blood flow between the arterial end and a venous end; a second housing encapsulating the first housing and forming a cavity between the first housing and the second housing, the cavity including a plurality of magnets configured to generate a magnetic field applied to the blood flow guided through the first housing; and at least one cannulation port arranged on a surface of the tubular body, the cannulation port configured for receiving needle punctures providing needle access to the first housing.

A magnetic vascular access system, in accordance with some exemplary embodiments of the present invention, may include: a magnetic vascular access device having a tubular body of biocompatible material including an arterial end adapted for arterial anastomosis to a portion of an artery, and a venous end adapted for venous anastomosis to a portion of a vein; a first housing running through the tubular body for guiding a blood flow between the arterial end and a venous end; a second housing encapsulating the first housing and forming a cavity between the first housing and the second housing, the cavity including a plurality of magnets configured to generate a magnetic field applied to the blood flow guided through the first housing; and at least one cannulation port arranged on a surface of the tubular body, the cannulation port configured for receiving needle punctures providing needle access to the first housing; and a magnetized graft collar configured to wrap around a portion of an arterial anastomosis or a venous anastomosis.

In some exemplary embodiments, a magnetic element comprises a circuitry configured to generate the magnetic field, the circuitry disposed on a surface of the cavity. In some exemplary embodiments, the magnetic element comprises a plurality of magnets configured in alternating polarities. In some exemplary embodiments, the magnetic element may include a a single magnet disposed about the flow. In some exemplary embodiments, the magnetic element may include a combination of both a circuitry configured to generate a magnetic field applied to the flow tube and one or more magnets disposed about the flow tube. In some exemplary embodiments, the plurality of magnets are configured in non-alternating polarities. In some embodiments, the magnets may be diametrically magnetized. In some embodiments, the magnets may be axially magnetized.

In some exemplary embodiments, a magnetic vascular access device in accordance with the present invention comprises a stand-alone device. In some exemplary embodiments, a magnetic vascular access device, in in accordance with the present invention, comprises a tubular body with one or more housing elements configured to receive at least a portion of a flow tube or commercially available graft.

As mentioned above, a system in accordance with exemplary embodiments of the present invention may include a magnetized graft collar configured to wrap around a portion of an arterial anastomosis or a venous anastomosis. In some exemplary embodiments, the magnetic graft collar may comprise of a mesh body including at least two layers of a flexible substrate; and a plurality of magnetic crystals disposed between the at least two layers of the flexible substrate. In some exemplary embodiments, silver and or copper components may be included with the magnetic crystals for their anti-microbial properties.

Various objectives and advantages of the present invention will become apparent from the following description taken in conjunction with the accompanying drawings wherein are set forth, by way of illustration and example, certain embodiments of this invention. The drawings submitted herewith constitute a part of this specification, include exemplary embodiments of the present invention, and illustrate various objects and features thereof.

BRIEF DESCRIPTION OF THE DRAWINGS

The system, apparatus, and the method for magnetizing a vascular access graft as disclosed herein are further described in terms of exemplary embodiments. These exemplary embodiments are described in detail with reference to the drawings, which have not necessarily been drawn to scale in order to enhance their clarity and improve understanding of the various embodiments of the invention. Furthermore, elements that are known to be common and well understood to those in the industry are not depicted in order to provide a clear view of the various embodiments of the invention. These embodiments are non-limiting exemplary embodiments, in which like reference numerals represent similar structures throughout the several views of the drawings. The drawings that accompany the detailed description can be briefly described as follows.

DETAILED DESCRIPTION OF THE INVENTION

Figure 1:
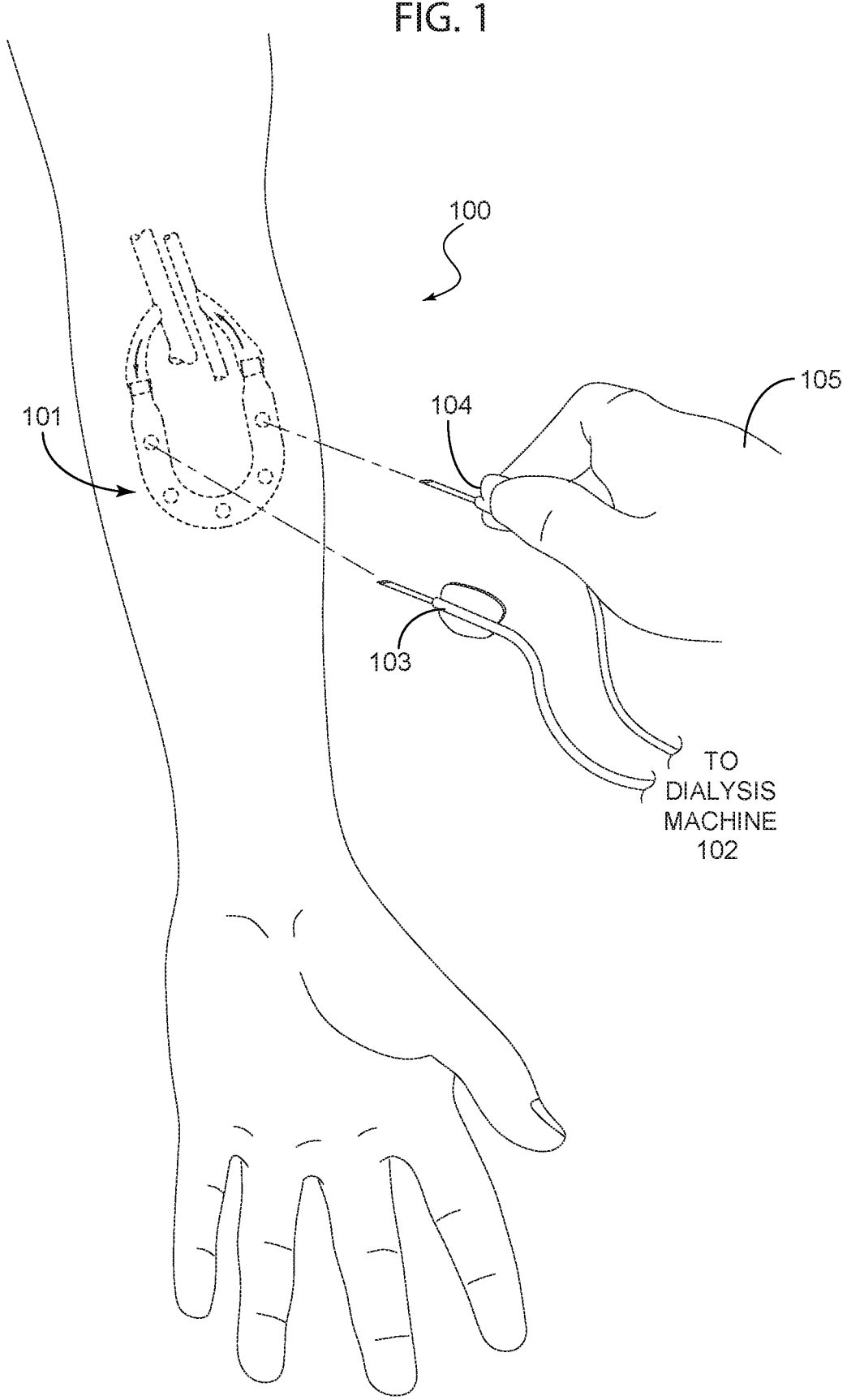
FIG. 1 illustrates a magnetic vascular access device implanted on a patient's arm, in accordance with exemplary embodiments of the present invention.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized, and changes may be made without departing from the scope of the invention. Wherever possible, the same reference numbers are used in the drawings and the following description to refer to the same or similar elements.

In the following detailed description, numerous specific details are set forth by way of examples in order to provide a thorough understanding of the relevant teachings. However, it should be apparent to those skilled in the art that the present teachings may be practiced without such details. In other instances, well known structures, components and/or functional or structural relationship thereof, etc., have been described at a relatively high-level, without detail, in order to avoid unnecessarily obscuring aspects of the present teachings.

Throughout the specification and claims, terms may have nuanced meanings suggested or implied in context beyond an explicitly stated meaning. Likewise, the phrase "in one embodiment/example" as used herein does not necessarily refer to the same embodiment and the phrase "in another embodiment/example" as used herein does not necessarily refer to a different embodiment. It is intended, for example, that claimed subject matter include combinations of example embodiments in whole or in part.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and or steps. Thus, such conditional language is not generally intended to imply that features, elements and or steps are in any way required for one or more embodiments, whether these features, elements and or steps are included or are to be performed in any particular embodiment.

The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present. The term "and or" means that "and" applies to some embodiments and "or" applies to some embodiments. Thus, A, B, and or C can be replaced with A, B, and C written in one sentence and A, B, or C written in another sentence. A, B, and or C means that some embodiments can include A and B, some embodiments can include A and C, some embodiments can include B and C, some embodiments can only include A, some embodiments can include only B, some embodiments can include only C, and some embodiments include A, B, and C. The term "and or" is used to avoid unnecessary redundancy. Similarly, terms, such as "a, an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

While exemplary embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the invention or inventions disclosed herein. Accordingly, the following detailed description does not limit the disclosure. Instead, the proper scope of the disclosure is defined by the appended claims.

The present disclosure relates to, among other things, a system and method for magnetizing a vascular access graft via a housing that also provides mechanical and structural protection from external compression. Exemplary embodiments of the present disclosure are described with reference to the drawings for illustration purposes and are not intended to limit the scope of the present disclosure.

Turning now to the figures, FIG. 1 illustrates a magnetic vascular access device implanted on a patient's arm, in accordance with exemplary embodiments of the present invention. More specifically, FIG. 1 depicts system 100, which includes a vascular access graft (device 101) that has been magnetized or configured with a magnetic element disposed over a flow tube that guides a blood flow between an arterial end and a venous end of device 101. Device 101 is shown implanted inside a patient's arm, as may be typically employed; however, a device 101 in accordance with the present invention may be implanted in other regions and used for other purposes without deviating from the scope of the present invention. In some exemplary embodiments, as shown in this figure, system 100 may also include a dialysis machine 102 to which needles 103 and 104 may be coupled in order to provide access to the blood flow guided by device 101. Typically, as will be discussed further below, needles 103 and 104—which may comprise metal or plastics or any other materials suitable for hypodermic needles—may access a flow tube within device 101 via one or more ports disposed on a surface of device 101, guided by an operator 105 such as a physician or other medical personnel.

Figure 2:
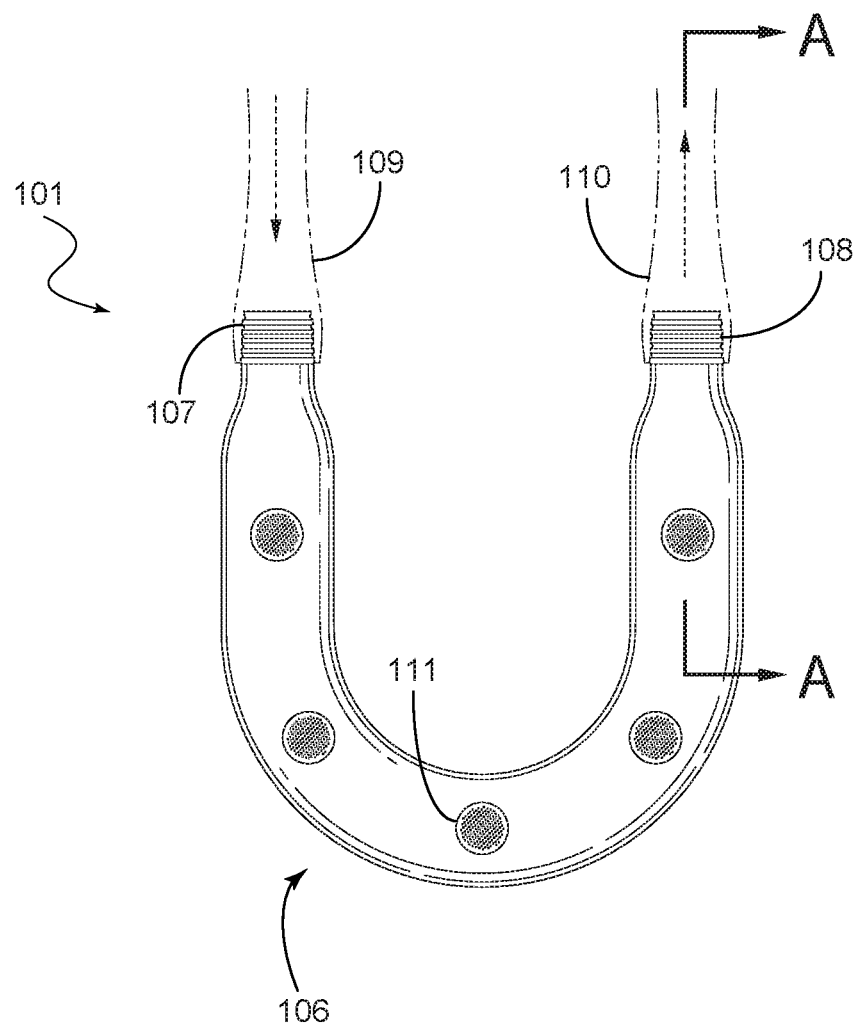
FIG. 2 illustrates a perspective view of a magnetic vascular access device in accordance with exemplary embodiments of the present invention.

Turning now to the next figure, FIG. 2 illustrates a perspective top view of a magnetic vascular access device in accordance with exemplary embodiments of the present invention. From this view, it may be appreciated that device 101 includes a body 106 that is generally tubular.

Body 106 of device 101 is generally a tubular body and may include different layers and components. In some exemplary embodiments, body 106 includes a housing, which may itself comprise of an outer housing and an inner housing. In some exemplary embodiments, body 106 includes one or more housings that include a cavity that encapsulates a flow tube adapted to guide plasma or blood therethrough (such cavity shown in more detail and discussed further below with reference to FIG. 3 and other figures). In exemplary embodiments, the housing encapsulates the flow tube in a manner such that a cavity is formed between an interior surface of the housing and an outer surface of the flow tube. Within the cavity, which may comprise of one or more chambers, one or more magnetic elements may be disposed. In some exemplary embodiments, the housing may be adapted to receive a commercially available flow tube or graft, or include a flow tube especially adapted for the housing, wherein the flow tube is adapted to guide blood from one terminal end of the flow tube to the other terminal end of the flow tube. Accordingly, body 106 encapsulates the one or more magnetic components in such a way so that one or more magnetic fields may be applied along a length of the flow tube within device 101.

Body 106 may be constructed of a wide range of generally biocompatible materials. For example, and without deviating from the scope of the present invention, in some exemplary embodiments, body 106 may be constructed using a hardened and malleable material, for example—and without limiting the scope of the present invention—a malleable metal. In exemplary embodiments, body 106 comprises of one or more malleable biocompatible materials suitable for implantation inside the human body. In some exemplary embodiments, body 106 is more flexible, while in other exemplary embodiments, body 106 is more rigid.

Body 106 may employ known technologies such as with grafts that provide immediate cannulation after placement (i.e. typically within 72 hours). These materials may be useful for standard patients to facilitate early catheter removal, but also have several niche applications that are valuable tools for the access surgeon, and can be cannulated immediately to eliminate the need for a dialysis catheter placement while the graft replacement heals.

Body 106 may be multi-layered. For example, and without limiting the scope of the present invention, body 106 may be constructed as a multi-layered component of device 101 suitable for housing a plurality of magnets disposed about a length of a flow tube therein. In exemplary embodiments, body 106 may be manufactured in both straight and looped or loopable configurations as will be discussed further below with reference to FIG. 13 and FIG. 14.

To facilitate anastomosis, device 101 includes an arterial end 107 and a venous end 108 with sewing areas on each terminal portion of the respective ends. As will be understood by person of ordinary skill in the art, arterial end 107 may be typically adapted for arterial anastomosis to a portion of an artery 109, and venous end 108 may be typically adapted for venous anastomosis to a portion of a vein 110, which may be preferably not shown.

To facilitate cannulation, body 106 typically includes a plurality of ports 111 such as cannulation ports that may include, in some exemplary embodiments, soft rings to resist compression and an inner gel that closes off needle holes. Known technologies for employing a wide range of ports may be employed without deviating from or limiting the scope of the present invention.

As mentioned briefly above and as will be discussed in the figures to follow, device 101 includes a magnetic element disposed within a portion of body 106, which is configured to apply a magnetic field to a flow tube that runs along an interior length of device 101, so that the magnetic field may be applied to blood flowing therein. The magnetic element may include one or more magnets, for example neodymium magnets, or may alternatively include a circuitry configured to generate a magnetic field applied to the flow tube, or a combination of one or more magnets as well as a circuitry configured to generate a magnetic field as disclosed above. It is propositioned that the magnetic field or fields applied to the flow tube generally disrupt atoms that make up the molecules that make up the clotting proteins or coagulation proteins, and ultimately, affect the protein function of said coagulation proteins to minimize build-up within the graft.

Figure 2A:
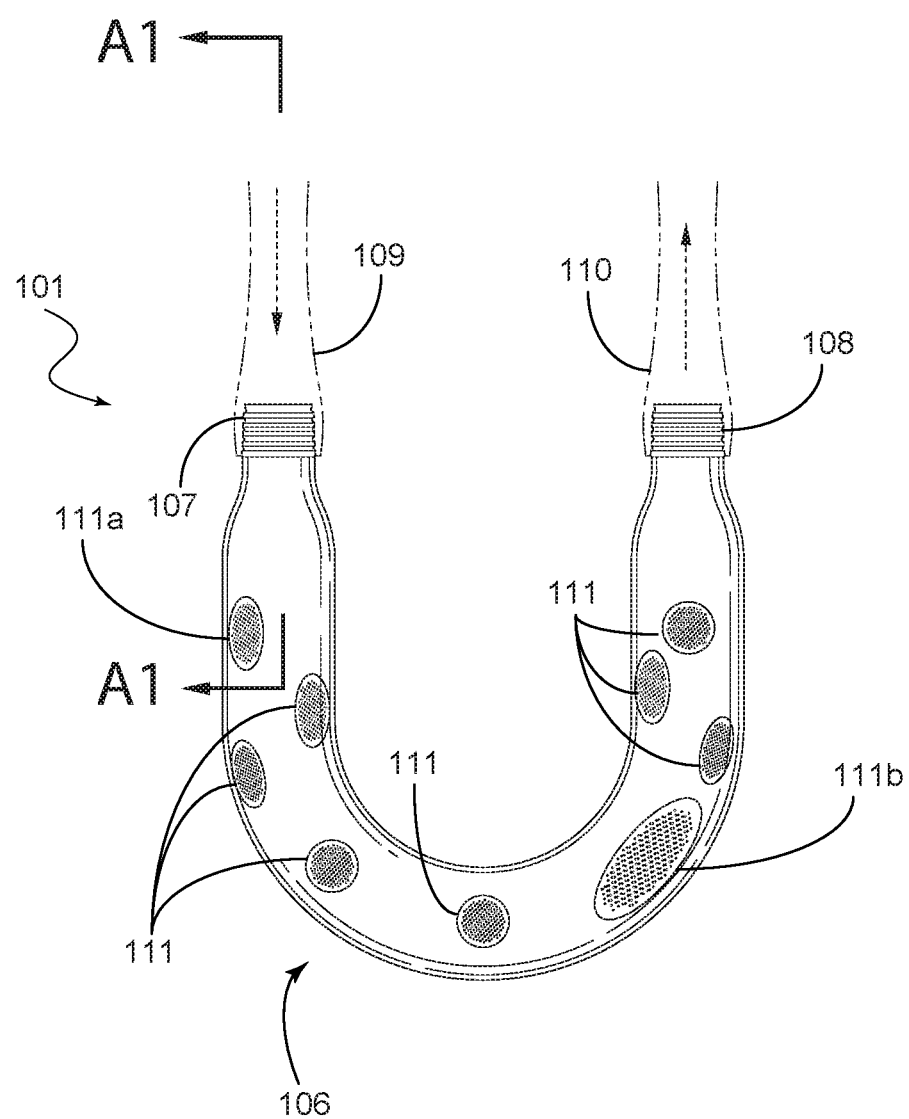
FIG. 2A illustrates a perspective view of a magnetic vascular access device in accordance with exemplary embodiments of the present invention.

Turning briefly to FIG. 2A, this view illustrates a perspective view of a magnetic vascular access device 101 in which several locations are shown, merely by way of example and in no way limiting the scope of the present invention, situated in various positions orientations, and having different sizes, along a surface of tubular body 106. Accordingly, this view is merely to illustrate that ports, such as port 111, port 111a, and port 111b, may be the same size, different sizes, the same or different shapes, and situated at various locations along the surface of the body in order to facilitate cannulation. Moreover, as will be explained further with reference to FIG. 3A, in some exemplary embodiments, at least one of a plurality of ports of device 100 may have a different purpose, such as for example facilitating the application of an anticoagulant medication (for example heparin) into the blood flow passing through a flow tube within device 101.

In one example, and without limiting the scope of the present invention, an exemplary embodiment may include a port 111a that may be a port that allows access to a chamber within a housing of device 101 that stores an anticoagulant medication so that the supply may be re-filled as it is depleted during use. As will be explained further below, such exemplary embodiment may employ a permeable membrane in order to timely release the anticoagulant medication into the flow tube of device 101. Furthermore, in exemplary embodiments, such port 111a may be situated towards or in proximity to the arterial end 107 adapted for arterial anastomosis to a portion of artery 109, in order to maximize the implementation of the anticoagulant medication into the blood flow throughout a majority of the flow tube therein.

In another example, and without limiting the scope of the present invention, an exemplary embodiment may include a port 111b that is enlarged and or shaped so as to maximize the ease in which the port is located by practitioner or medical personnel during cannulation.

In yet another example, and without limiting the scope of the present invention, an exemplary embodiment may include a plurality of ports 111 that are situated in various locations throughout a surface of body 106 of device 101 so as to maximize the ease in which any one f the plurality of ports 111 is located by a practitioner or medical personnel during cannulation.

In yet another example, and without limiting the scope of the present invention, an exemplary embodiment may include a combination of one or more of port 111, port 111a, and port 111b so as to facilitate the application of an anticoagulant medication, and or maximize the ease in which any one of the plurality of ports is located by a practitioner or medical personnel during cannulation.

As will be appreciated by those skilled in the art, various configurations with alternative or combination of different types of ports may be possible without deviating form the scope of the present invention.

Figure 3:
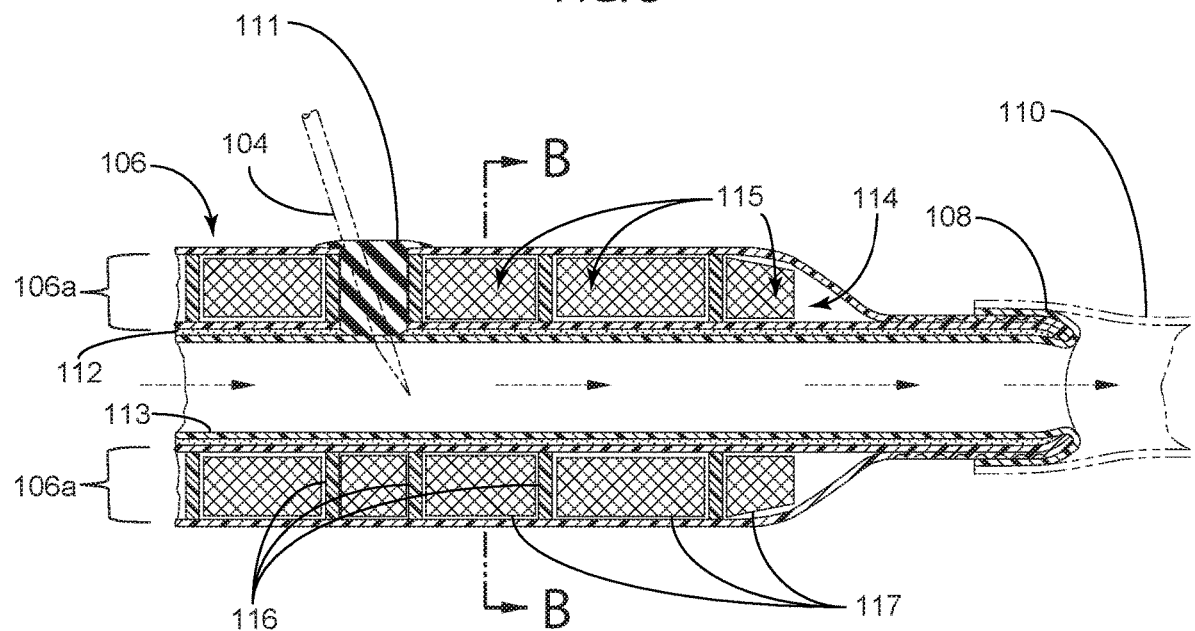
FIG. 3 illustrates a cross-sectional view of a magnetic vascular access device in accordance with exemplary embodiments of the present invention.

Turning now to the next figure, FIG. 3 illustrates a cross-sectional view of the magnetic vascular access device 101, in accordance with exemplary embodiments of the present invention. More specifically, FIG. 3 depicts a cross-sectional view along the line segment A-A depicted in FIG. 2. This view shows a portion of the tubular body 106 including one of the terminal ends or the venous end 108.

From this view, it may be appreciated that tubular body 106 may comprise a housing 106a, 112 running through the tubular body 106 and adapted to house a flow tube 113 for guiding a blood flow between the arterial end 107 and the venous end 108. Furthermore, a cavity 114 is generally formed within the housing 106a, 112 and adapted to encapsulate the flow tube 113, the cavity 114 including a magnetic element 117 configured to apply a magnetic field to the blood flow guided through the flow tube 113. Moreover, at least for vascular access purposes, device 101 may further include at least one cannulation port 111 (and or 111a, and or 111b) arranged on a surface of the tubular body 106, the cannulation port(s) port 111 (and or 111a, and or 111b) configured for receiving needle punctures providing needle access to an interior of the housing 106a, 112 and or an interior of the flow tube 113.

In some exemplary embodiments, the housing 106a, 112 may be constructed as a single integral component. However in other exemplary embodiments, the housing 106a, 112 may be constructed as a first housing, for example an inner housing 112 that is adapted to house a flow tube 113 that is configured to guide a blood flow from arterial end 107 to venous end 108, and a second housing, for example an outer housing 106a formed between an outer surface of the inner housing 112 and an interior surface of the tubular body 106. Wherein outer housing 106a forms cavity 114, in which one or more chambers 115 may be formed (with for example dividers 116) to house a magnetic element 117, which in some exemplary embodiments may include a plurality of magnets. The outer housing 106a may include at least one or more ports, such as port 111.

In exemplary embodiments, these ports, including port 111 may be a cannulation port that includes soft rings to resist compression and an inner gel that closes off needle holes, so that it is configured to provide needle 104 (for example) access to the flow tube 113. As mentioned above, known technologies for employing a wide range of ports may be employed without deviating from or limiting the scope of the present invention.

Flow tube 113 may be constructed of materials typically used with vascular access grafts, so that any number of technologies may be implemented for flow tube 113 without deviating from the scope of the present invention. For example, and without limitation, flow tube 113 may comprise of bovine carotid artery. In some exemplary embodiments, flow tube 113 may comprise polytetrafluoroethylene (ePTFE). In some exemplary embodiments, flow tube 113 may comprise of tissue-engineered components. Similarly, any known technologies may be implemented into housing 106a, 112—and or either the inner housing and or the outer housing—and components thereof without limiting or deviating from the scope of the present invention.

Moreover, it should be appreciated that in some embodiments device 101 comprises a stand-alone vascular access device so that flow tube 113 may be constructed especially to be permanently housed within the housing of tubular body 106 of device 101. However, in exemplary embodiments, device 101 is configured to retrofit an existing vascular access graft and as such, in those exemplary embodiments, flow tube 113 may be a commercially available vascular access graft that is housed within the housing or housings of device 101.

Accordingly, in some exemplary embodiments, a magnetic vascular access device in accordance with the present invention comprises a stand-alone device, and in other exemplary embodiments, a magnetic vascular access device in in accordance with the present invention comprises a tubular body with one or more housing elements configured to receive a commercially available vascular access graft.

Thus, in some exemplary embodiments, device 101 may comprise a bovine carotid artery graft typically including a collagen matrix that is a non-antigenic and includes a de-cellularised conduit. In some exemplary embodiments, device 101 may comprise a high elasin-to-collegen ratio for improved pulsitility. For example, and in no way limiting the scope of the present invention, device 101 may implement a de-cellularised natural conduit or flow tube 113 made from bovine mesenteric vein configured with known technologies so that it may be stored on the shelf and can be rinsed immediately prior to use.

Accordingly, in some exemplary embodiments, a magnetic vascular access device may include: a tubular body 106 including an arterial end 107 adapted for arterial anastomosis to a portion of an artery, and a venous end 108 adapted for venous anastomosis to a portion of a vein; a flow tube 113 running through the tubular body for guiding a blood flow between the arterial end 107 and a venous end 108; an outer housing 106a encapsulating the flow tube 113 and forming a cavity 114 between an exterior of the flow tube 113 and the outer housing 106a, the cavity 114 including a magnetic element 117 configured to generate a magnetic field applied to the blood flow guided through the flow tube 113; and at least one port 111 arranged on a surface of the tubular body 106, the port configured for providing needle access to the flow tube.

In some exemplary embodiments, the magnetic element 117 comprises a circuitry configured to generate the magnetic field, the circuitry disposed on a surface of the cavity. In some exemplary embodiments, the magnetic element 117 comprises a plurality of magnets configured in alternating polarities. In some exemplary embodiments, the magnetic element 117 comprises a combination of one or more magnets as well as a circuitry configured to generate a magnetic field as disclosed above. In some exemplary embodiments, the plurality of magnets are configured in non-alternating polarities. In some embodiments, the magnets may be diametrically magnetized. In some embodiments, the magnets may be axially magnetized. Some of these types of magnets that may be housed within body 106 of device 101 will be discussed in more detail below.

In yet other exemplary embodiments, a magnetic vascular access device may include: a tubular body 106 of biocompatible material including an arterial end 107 adapted for arterial anastomosis to a portion of an artery, and a venous end 108 adapted for venous anastomosis to a portion of a vein; a first housing 112 running through the tubular body 106 adapted to house a flow tube 113 for guiding a blood flow between the arterial end 107 and a venous end 108; a second housing 106a encapsulating the first housing 112 and forming a cavity 114 between the first housing 112 and the second housing 106a, the cavity 114 including a plurality of magnets 117 configured to generate a magnetic field applied to the blood flow guided through the flow tube 113 within housing 112; and at least one cannulation port 111 arranged on a surface of the tubular body 106, the cannulation port 111 configured for receiving needle punctures providing needle access to the first housing and more particularly the blood flow therein.

Figure 3A:
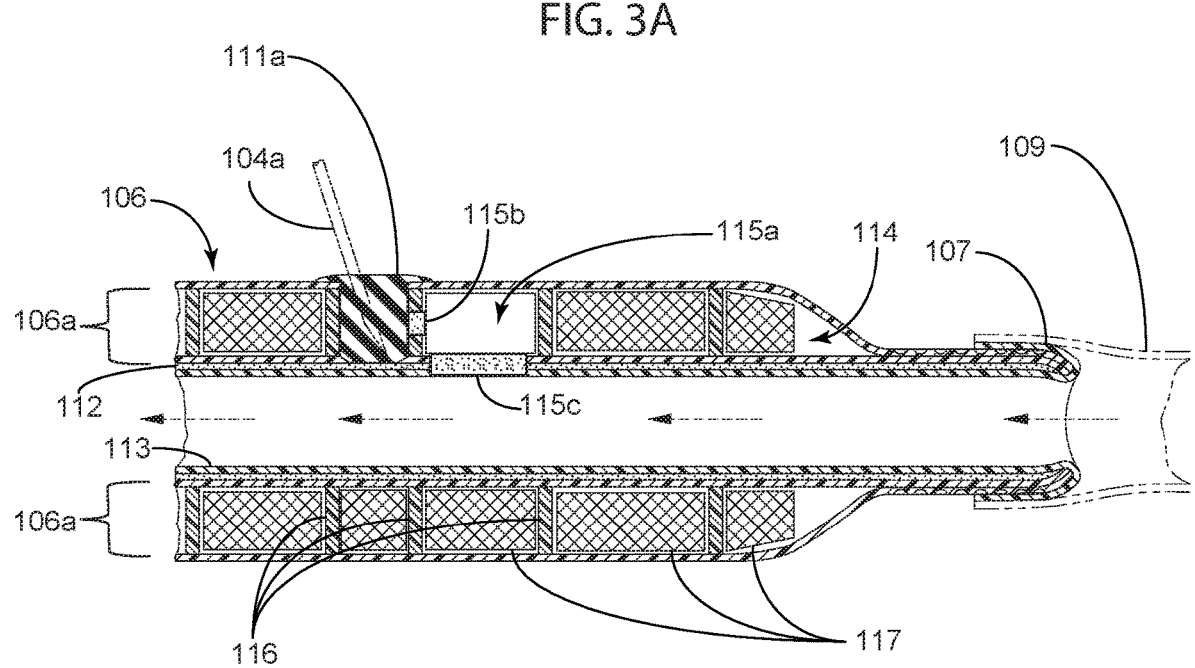
FIG. 3A illustrates a cross-sectional view of a magnetic vascular access device in accordance with exemplary embodiments of the present invention.

Briefly turning to FIG. 3A, a cross-sectional view of a magnetic vascular access device in accordance with exemplary embodiments of the present invention is illustrated. More specifically, FIG. 3A depicts a cross-sectional view along the line segment A1-A1 depicted in FIG. 2A. This view shows a portion of the tubular body 106, according to the embodiment of FIG. 2A, including one of the terminal ends or the arterial end 109.

As mentioned above, in this embodiment, at least one of a plurality of ports of device 100, for example port 111a, may facilitate the application of an anticoagulant medication such as heparin into the blood flow passing through flow tube 113 within device 101. In this embodiment, port 111a may not access flow tube 113 but rather limit access to a chamber 115a within cavity 114 in order to facilitate the storage and delivery of an anticoagulant medication. Moreover, in this manner, a supply of the anticoagulant medication may be re-filled as it is depleted during use by way of an access 115b between port 111a and chamber 115a. In exemplary embodiments, chamber 115a may employ a permeable membrane 115c in order to facilitate the timely release of the anticoagulant medication stored therein into flow tube 113 of device 101. As shown in FIG. 2A and FIG. 3A, in exemplary embodiments, port 111a is situated in proximity to the arterial end 107 adapted for arterial anastomosis to a portion of artery 109, in order to maximize the implementation of the anticoagulant medication into the blood flow throughout a majority of the length of flow tube 113. In another embodiment chamber 115a and another chamber (not shown, but situated somewhere towards the middle of body 106, may be filled with short acting anticoagulation medication such as a short acting heparin, that leaks out at a constant rate (i.e. microliters per hour). In some exemplary embodiments, chamber 115a may be refillable (so that port 111a is employed as shown) or chamber 115a may be sealed. In either embodiment in which the short acting anticoagulation medication is employed however, chamber 115a may include silver and/or copper elements that may also contribute to a transmission of the medication rate that is acceptable. For example and without deviating from the scope of the present invention, a metallic configuration, may include both silver and copper ions configured to "leak" or "part" from the base supply chunk and "leach" onto the surface of flow tube 113 (i.e. via permeable membrane 115c), and thus ultimately, to the plasma (whole blood essential), at a safe but effective dose. One of the benefits of such embodiments, is the anti-microbial nature of those two metals, as is well known and used extensively in the medical field. In this way, device 101 may incorporate both anti-thrombosis and the anti-microbial enhancements that help extend the life of flow tube 113 (i.e. whether a commercially available graft or integra component of device 101), and subsequently, the life and function of the patient using the device.

Figure 4:
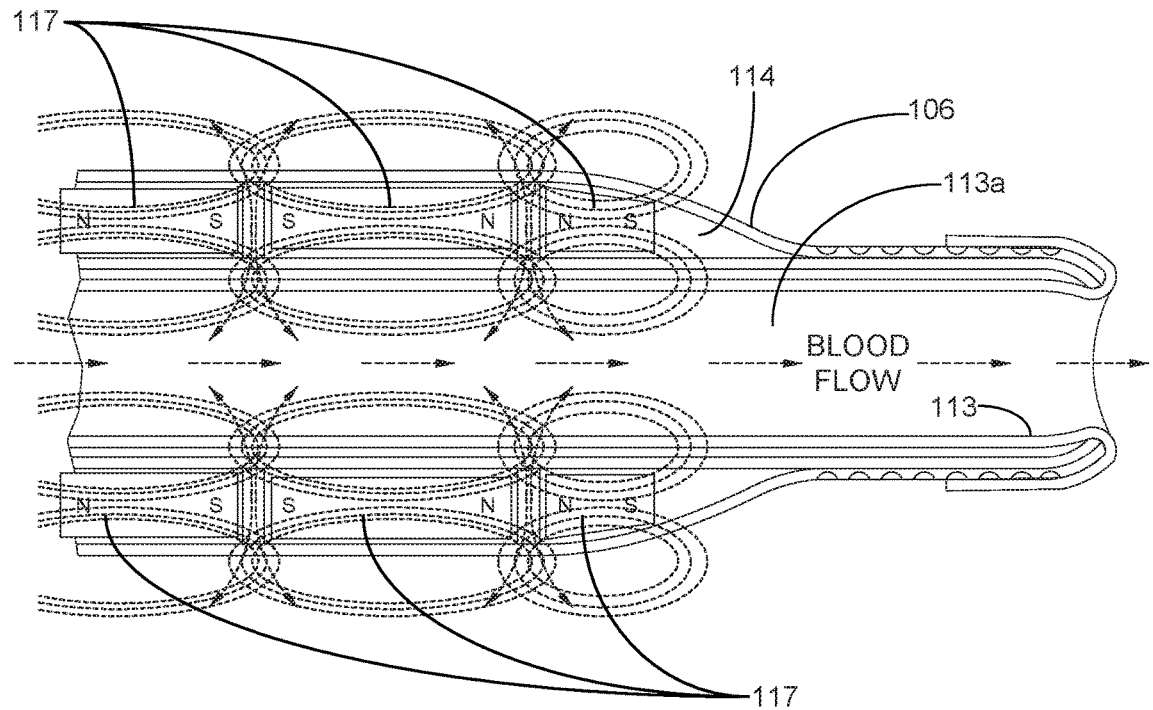
FIG. 4 illustrates a cross-sectional view of a magnetic vascular access device in accordance with exemplary embodiments of the present invention.

Turning now to the next figure, FIG. 4 illustrates a cross-sectional view of a magnetic vascular access device in accordance with exemplary embodiments of the present invention. More specifically, this view depicts exemplary magnetic fields emitting from a plurality of magnets 117 housed within cavity 114 of the tubular body 106 of device 101. As explained above, it is propositioned that the magnetic field or fields applied to the flow tube 113, and more specifically along a lumen 113a of flow tube 113, generally disrupt the molecules that make up the coagulation proteins, and ultimately, affect the protein function of said coagulation proteins to minimize build-up within device 101.

More specifically, it is proposed that because any "flow" of electrons, or any "current" will have its own magnetic field, by definition, then any blood flow passing through lumen 113a of flow tube 113 within inner housing 112 will have its own magnetic field. As this blood flow's magnetic field (typically undisturbed within the body) is now introduced through flow tube 113 to at least one other competing magnetic field generated from the one or more magnets 117 inside cavity 114 of outer housing 106a, the effect of the competing magnetic fields on the electrons in the blood flow is to causes protein dysfunction. It is further proposed that this disruption that causes protein dysfunction (so that for example coagulation is minimized), is short-lived and effective only during the exposure of the blood flow to the competing magnetic field within the flow tube, so that upon exiting device 101, the blood flow reverts back to a normal state.

Figure 5A:
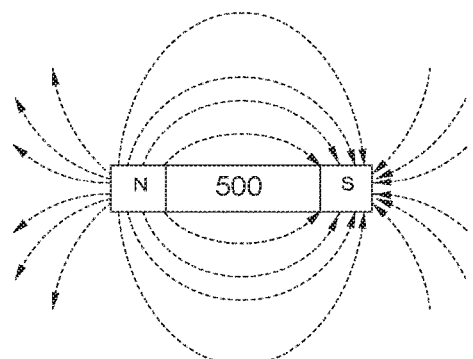
FIG. 5(a)-FIG. 5(c) illustrate magnets showing the direction of their magnet fields.
Figure 5B:
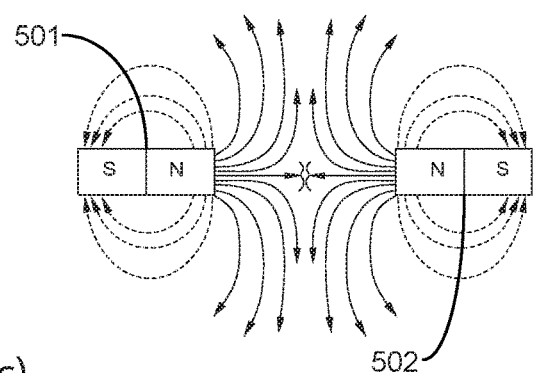
Figure 5C:
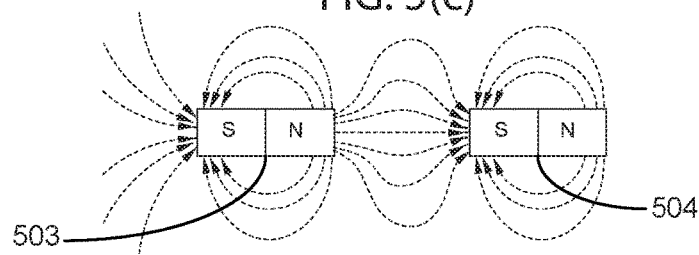

Next, FIG. 5(*a*)-FIG. 5(*c*) illustrate magnets showing the direction of their magnet fields. As a person of ordinary skill in the art will appreciate, depending on the orientation and configuration within the device of the various magnets 500, 501, 502, 503, and 504, different alternating or non-alternating polarities may be achieved to generate different magnetic fields applied to the flow tube within body 106. The next set of figures shows a variety of magnet types that may be used in accordance with the present invention. That is, one or more of these following types of magnets may be implemented into body 106 of device 101. In some embodiments, only one type of magnet is used throughout body 106. In another exemplary embodiment, more than one type of magnet is employed throughout an interior of body 106 of device 101.

Figure 6A:
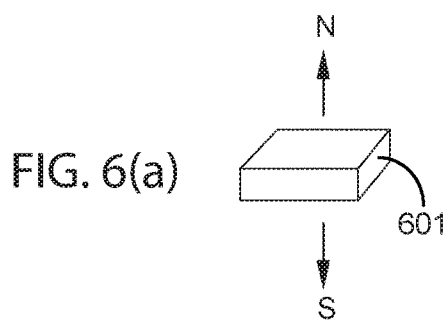
FIG. 6(a)-FIG. 6(b) illustrate a plurality of magnets having various shapes that may be implemented within a magnetic vascular access device in accordance with exemplary embodiments of the present invention.
Figure 6B:
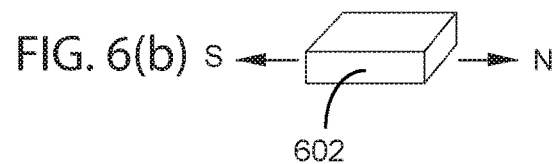

For example, and without limiting the scope of the present invention, FIG. 6(*a*)-FIG. 6(*b*) illustrate a plurality of bar magnets that may be implemented within a magnetic vascular access device in accordance with exemplary embodiments of the present invention. More specifically, FIG. 6(*a*) shows a cube or rectangular magnet 601 that has been magnetized through its thickness. FIG. 6(*b*) shows a similar cubed or rectangular magnet 602 that has been magnetized through its length or width. Depending on the desired configuration one or more of these bar magnets may be disposed throughout the housing of device 101 in order to achieve alternating polarities or non-alternating polarities.

Figure 7A:
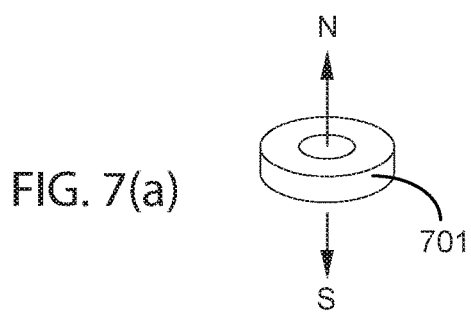
FIG. 7(a)-FIG. 7(b) illustrate a plurality of magnets having various shapes that may be implemented within a magnetic vascular access device in accordance with exemplary embodiments of the present invention.
Figure 7B:
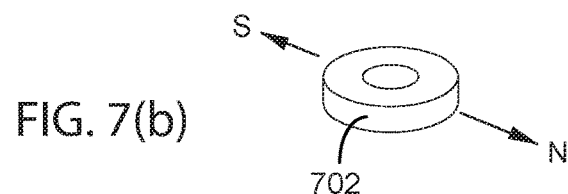

For example, and without limiting the scope of the present invention, FIG. 7(*a*)-FIG. 7(*b*) illustrate another set of magnets having different shapes that may be implemented within a magnetic vascular access device in accordance with exemplary embodiments of the present invention. More specifically, FIG. 7(*a*) shows a disc magnet 701 that may be axially magnetized or magnetized through the length or thickness of the magnet with strongest points on the flat faces. FIG. 7(*b*) shows a disc magnet 702 that is instead magnetized through the diameter so that the strongest points are on the curved surfaces. Moreover, disc magnet 702 may be a single piece magnet or a multi-piece magnet such as multiple arc magnets that are diametrically magnetized from the inside radius through the outside radius so that the strongest points are the inside curved surfaces of the disc opening. Depending on the desired configuration one or more of these disc magnets may be disposed throughout the housing of device 101 in order to achieve alternating polarities or non-alternating polarities.

Figure 8A:
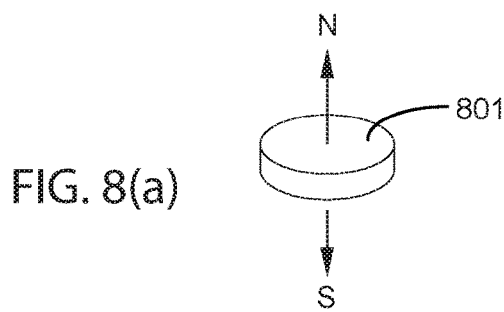
FIG. 8(a)-FIG. 8(b) illustrate a plurality of magnets having various shapes that may be implemented within a magnetic vascular access device in accordance with exemplary embodiments of the present invention.
Figure 8B:
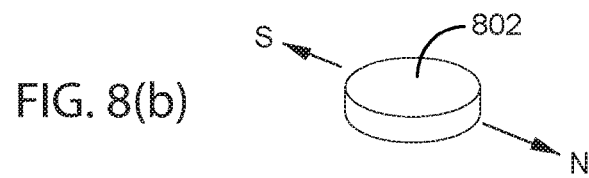

For example, and without limiting the scope of the present invention, FIG. 8(*a*)-FIG. 8(*b*) illustrate another set of magnets having different shapes that may be implemented within a magnetic vascular access device in accordance with exemplary embodiments of the present invention. More specifically, FIG. 8(*a*) shows a cylinder magnet 801 that may be axially magnetized or magnetized through the length or thickness of the magnet with strongest points on the flat faces. FIG. 8(*b*) shows a cylinder magnet 802 that is instead diametrically magnetized through the diameter so that the strongest points are on the curved surfaces. Depending on the desired configuration one or more of these disc magnets may be disposed throughout the housing of device 101 in order to achieve alternating polarities or non-alternating polarities.

Figure 9A:
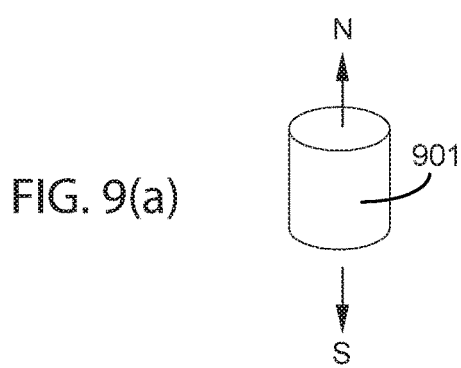
FIG. 9(a)-FIG. 9(b) illustrate a plurality of magnets having various shapes that may be implemented within a magnetic vascular access device in accordance with exemplary embodiments of the present invention.
Figure 9B:
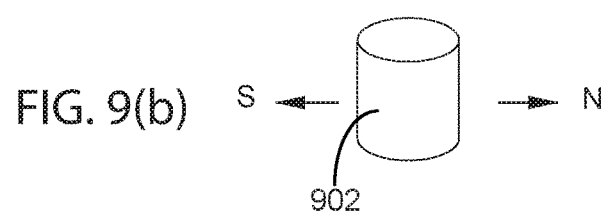

For example, and without limiting the scope of the present invention, FIG. 9(*a*)-FIG. 9(*b*) illustrate another set of magnets having different shapes that may be implemented within a magnetic vascular access device in accordance with exemplary embodiments of the present invention. More specifically, FIG. 9(*a*) shows another type of cylinder magnet 901 that may be axially magnetized or magnetized through the length or thickness of the magnet with strongest points on the flat faces, and FIG. 9(*b*) shows a similar cylinder magnet 902 that is instead diametrically magnetized through the diameter so that the strongest points are on the curved surfaces.

Figure 10:
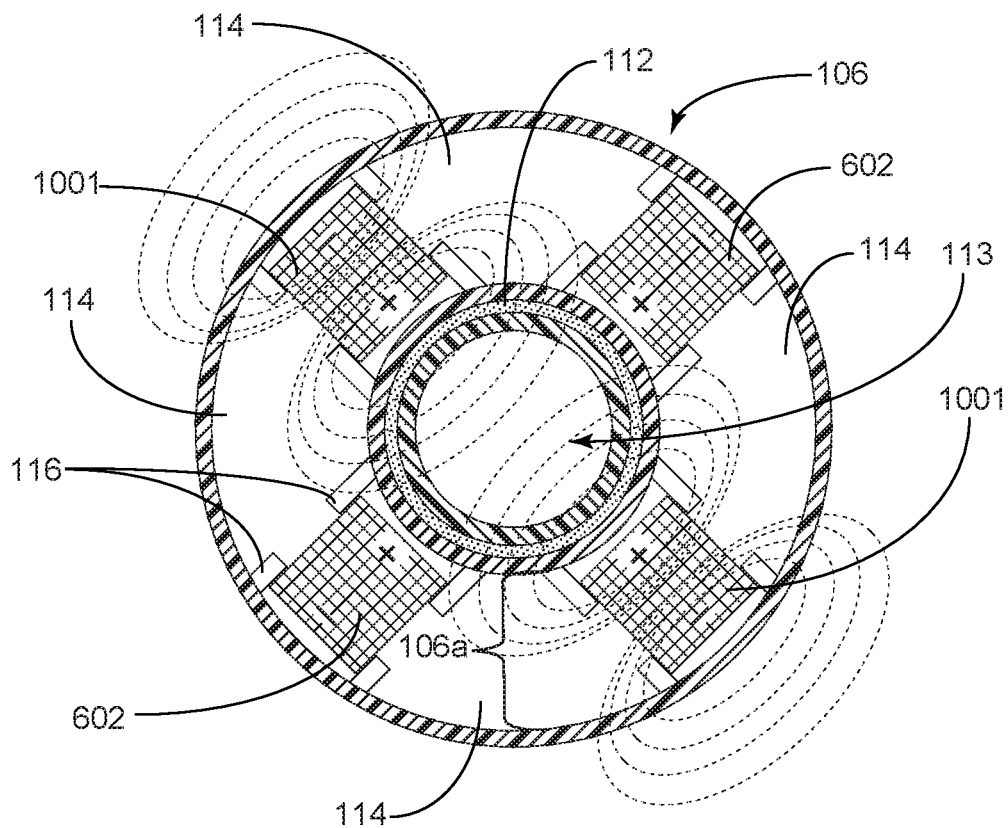
FIG. 10 illustrates a cross-sectional view of a tubular body of a magnetic vascular access graft in accordance with exemplary embodiments of the present invention, this view showing multiple staggered magnets disposed about a portion of a flow tube of the magnetic vascular access device.
Figure 11:
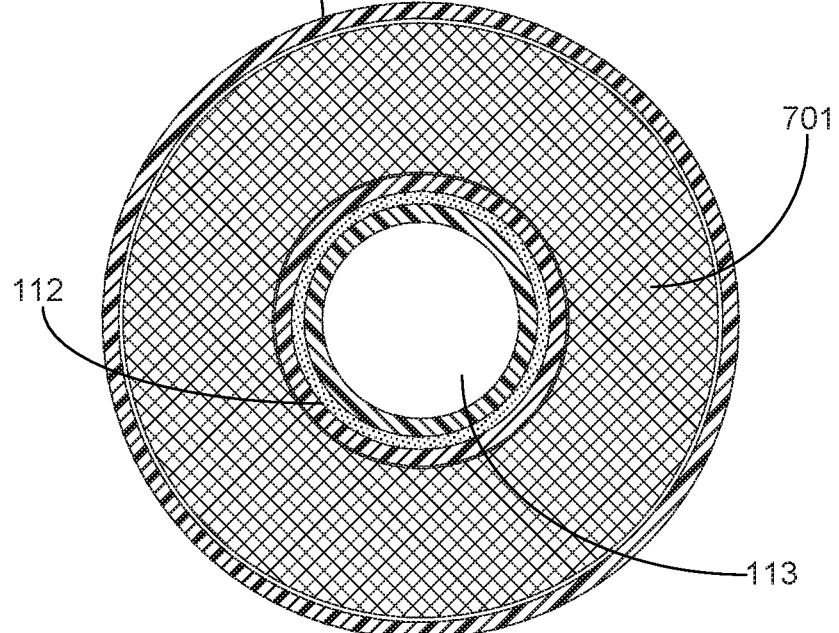
FIG. 11 illustrates a cross-sectional view of a tubular body of a magnetic vascular access graft in accordance with exemplary embodiments of the present invention, this view showing a single disc magnet disposed about a portion of a flow tube of the magnetic vascular access device.

Turning now to the next two figures, FIG. 10 illustrates a cross-sectional view of a tubular body of a magnetic vascular access graft in accordance with exemplary embodiments of the present invention, this view showing multiple magnetic components disposed about a portion of a flow tube of the magnetic vascular access device; and FIG. 11 illustrates a cross-sectional view of a tubular body of a magnetic vascular access graft in accordance with exemplary embodiments of the present invention, this view showing a magnetic component disposed about a portion of a flow tube of the magnetic vascular access device.

More specifically, FIG. 10 depicts an exemplary cross-sectional view illustrating how cavity 114 may be configured with a plurality of support members or dividers 116 that secure each one of a plurality of magnetic components, such as a circuitry 1001 and magnets 602. In this embodiment, the plurality of magnetic components may comprise a plurality of magnets 602 as well as a circuitry 1001 configured to generate a magnetic field, wherein the magnetic components emit a plurality of magnetic fields that are applied to the flow tube 113. Spaces in between each of the plurality of magnetic components may be empty or may comprise of non-electrically conductive spacers situated between respective magnetic components. In some exemplary embodiments, only a circuitry 1001 is disposed within cavity 114.

FIG. 11 depicts an exemplary cross-sectional view illustrating how cavity 114 may house a single disc magnet 702. As briefly mentioned above with reference to FIG. 7(*b*), disc magnet 702 may be a single piece magnet or a multi-piece magnet such as multiple arc magnets that are diametrically magnetized from the inside radius through the outside radius so that the strongest points are the inside curved surfaces of the disc opening. In exemplary embodiments, device 101 includes at least one cross-section that includes multiple arc magnets that are diametrically magnetized from the inside radius through the outside radius so that the strongest points are the inside curved surfaces of the disc opening along an external surface of flow tube 113 within housing 112.

In some exemplary embodiments, FIG. 10 is a first cross-section of the tubular body 106, and FIG. 11 is second cross-section of the tubular body 106 so that various types of magnets and magnet configurations are disposed along a length of flow tube 113.

Figure 12:
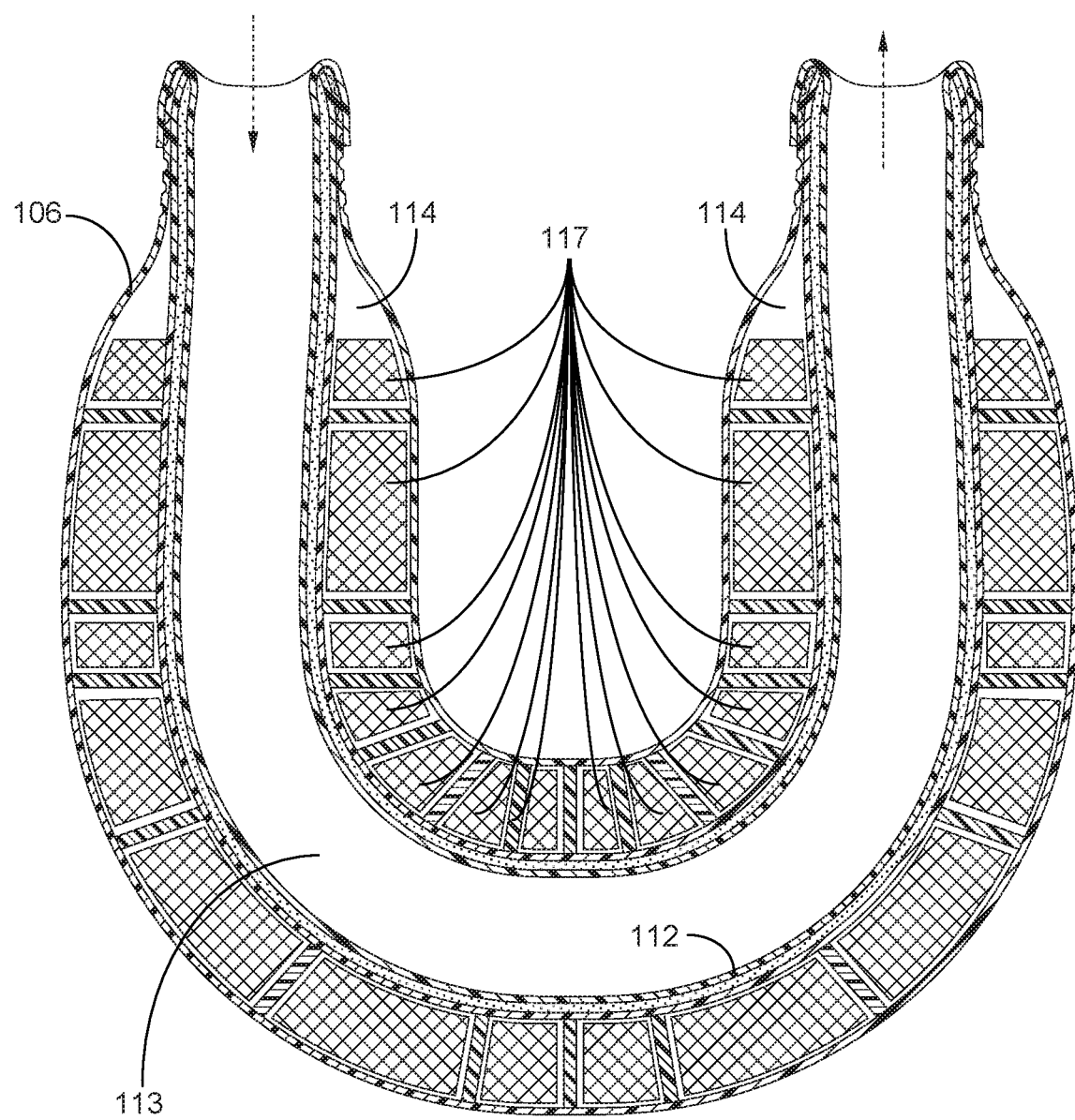
FIG. 12 illustrates a cross-sectional top view of a magnetic vascular access device depicting possible configuration of a magnetic element in accordance with exemplary embodiments of the present invention.

Turning now to the next figure, FIG. 12 illustrates a cross-sectional top view of a magnetic vascular access device depicting possible configuration of a magnetic element in accordance with exemplary embodiments of the present invention. From this view, what was mentioned above with reference to FIGS. 10 and 11 may be better appreciated. That is, while some of the plurality of magnets 117 may comprise disc magnets that take up a particular cross-section, other types of magnets may be disposed along the cavity 114 within the various chambers created therewith, for example, non-electrically charged spacers. In some exemplary embodiments, instead of every slot along cavity 114 being filled with a magnet, alternating slots may be filled with non-electrically charged spacers. In some exemplary embodiments, instead of every slot along cavity 114 being filled with a magnet in the same orientation, alternating slots may be filled with magnets in a staggered or alternating configuration. In other embodiments, the magnets fill up all slots or chambers within cavity 114 so that there are no spacers (as shown in FIG. 12. Accordingly, various configurations may be employed so that different competing magnetic fields may be applied to flow tube 113 so as to cause a maximum disruption to the molecules that make up the coagulation proteins, and ultimately, affect the protein function of said coagulation proteins to minimize build-up within device 101.

Figure 13:
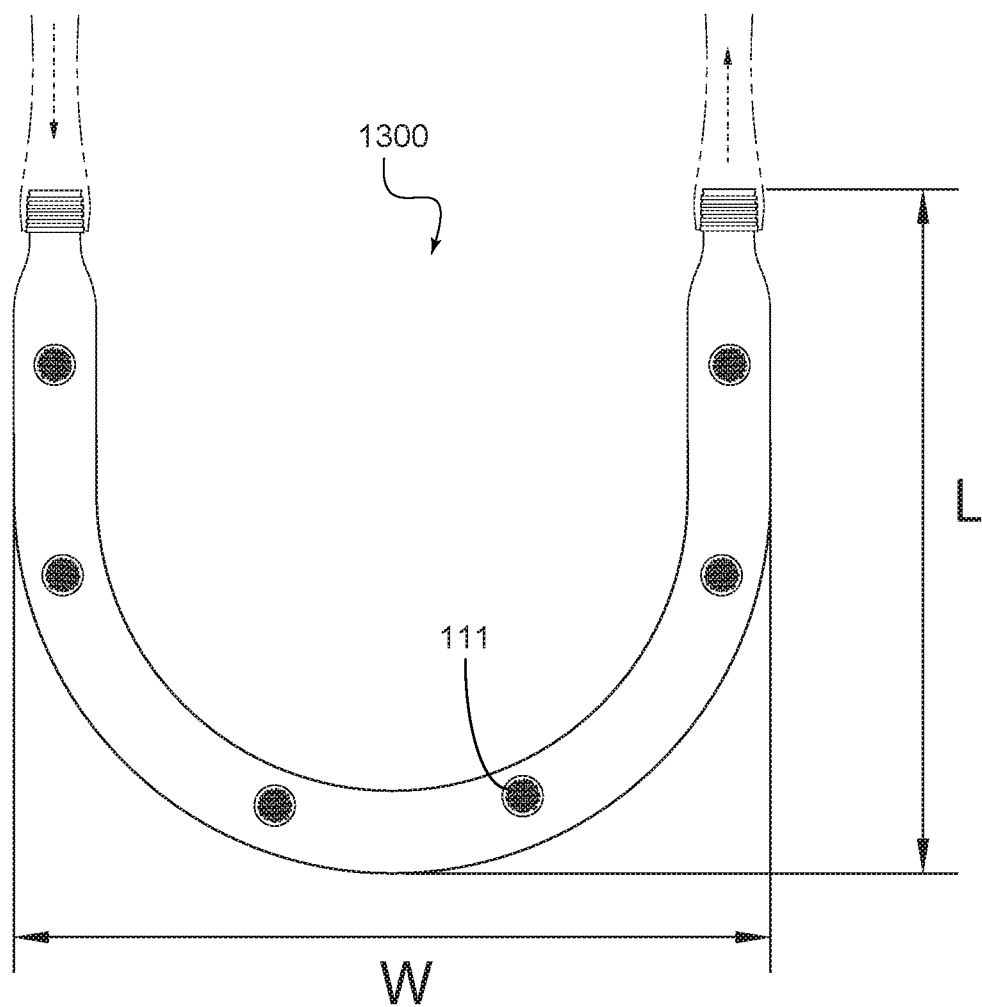
FIG. 13 illustrates a perspective top view of a magnetic vascular access device in accordance with exemplary embodiments of the present invention, wherein the tubular body forms a U-shape between the arterial end and the venous end.
Figure 14:
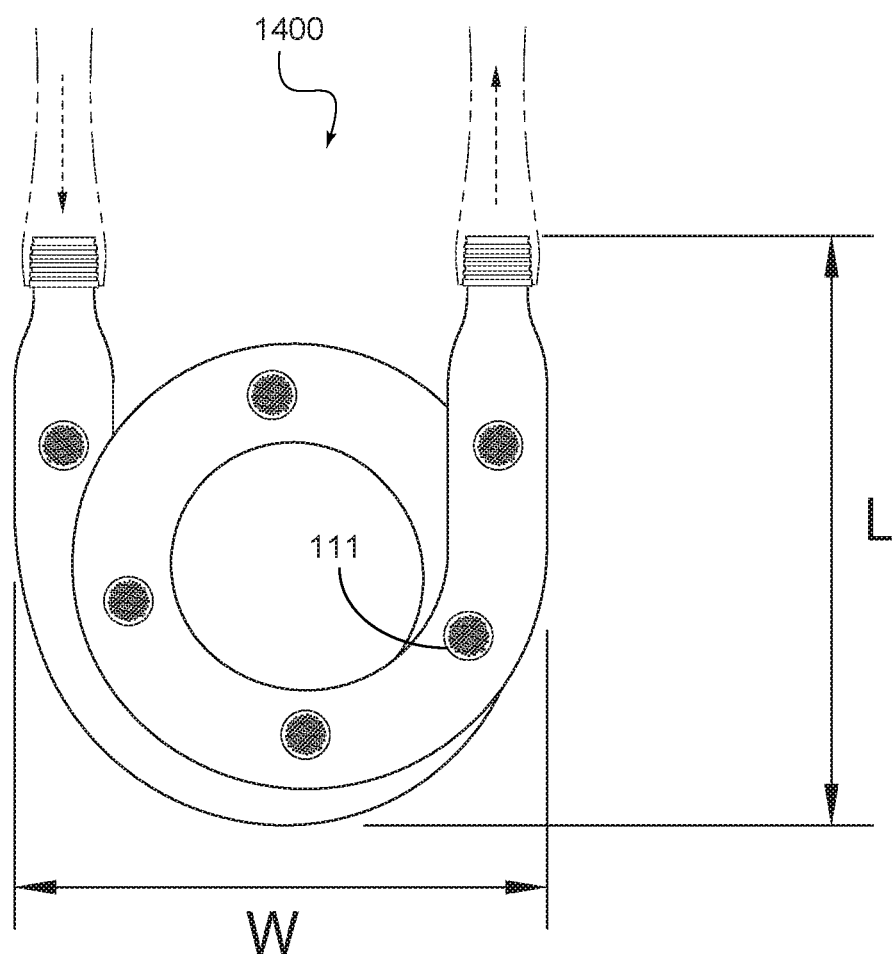
FIG. 14 illustrates a perspective top view of a magnetic vascular access device in accordance with exemplary embodiments of the present invention, wherein the tubular body is configured to spiral between the arterial end and the venous end to allow adjustment of a length and a width of the tubular body.

The next two figures illustrate how varying lengths and shapes may be employed with a magnetic vascular access graft in accordance with the present invention. FIG. 13 illustrates a perspective top view of a magnetic vascular access device, wherein the tubular body forms a U-shape between the arterial end and the venous end. More specifically, the total length of device 1300 is such that only a U-shaped curve may be formed between an arterial end and a venous end of the tubular body of the device, and a length L is approximate to a width W of the device. FIG. 14 illustrates a perspective top view of a magnetic vascular access device in accordance with another exemplary embodiments of the present invention, wherein the tubular body is configured to spiral between the arterial end and the venous end to allow adjustment of a length and a width of the tubular body. More specifically, the total length of device 1400 is such that multiple curves may be stacked in a spiral formed between an arterial end and a venous end of the tubular body of the device. In this case, a length L and a width W of the device may be adjusted.

Figure 15A:
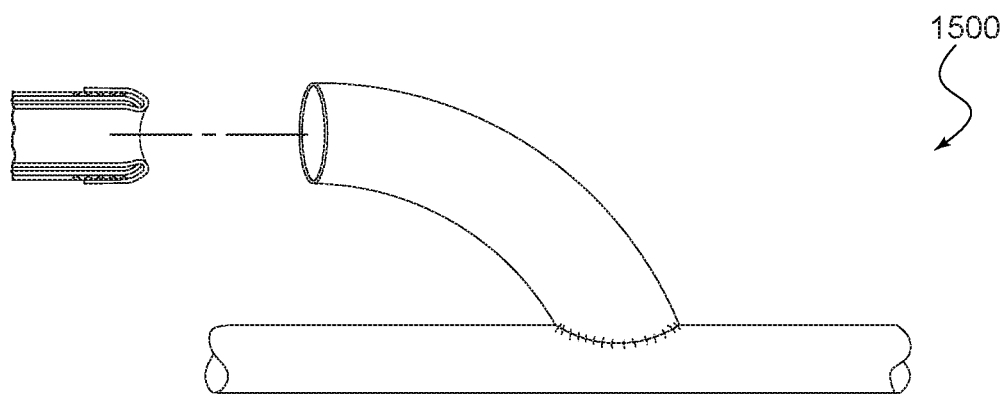
FIG. 15(a)-FIG. 15(b) illustrate a method of connecting a magnetic vascular access device to the vasculature of a patient in accordance with practice of the present invention.
Figure 15B:
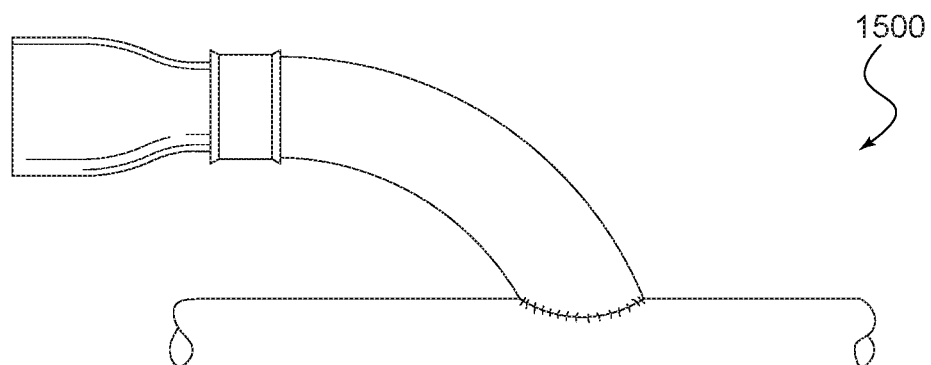

FIG. 15(a)-FIG. 15(b) illustrate a method of connecting a magnetic vascular access device to the vasculature of a patient in accordance with practice of the present invention. As a person of ordinary skill in the art may appreciate, any known method of surgically connecting vessels to device 1500 or otherwise arterial or venous anastomosis, may be practiced by an operator without deviating from the scope of the present invention. However, it is proposed that a surgical or operating microscope may be employed by the operator in order to facilitate such procedure.

Further, as will be explained in more detail below with reference to FIG. 16-FIG. 18, a method of implanting a system in accordance with the present invention may include not only implanting a magnetic vascular access device, but also implanting a magnetized graft collar configured to wrap around a portion of an arterial anastomosis or a venous anastomosis in order to continue the therapeutic effects of the magnetic fields into the junctions between device 101 and the vascular it is connected thereto.

Figure 16:
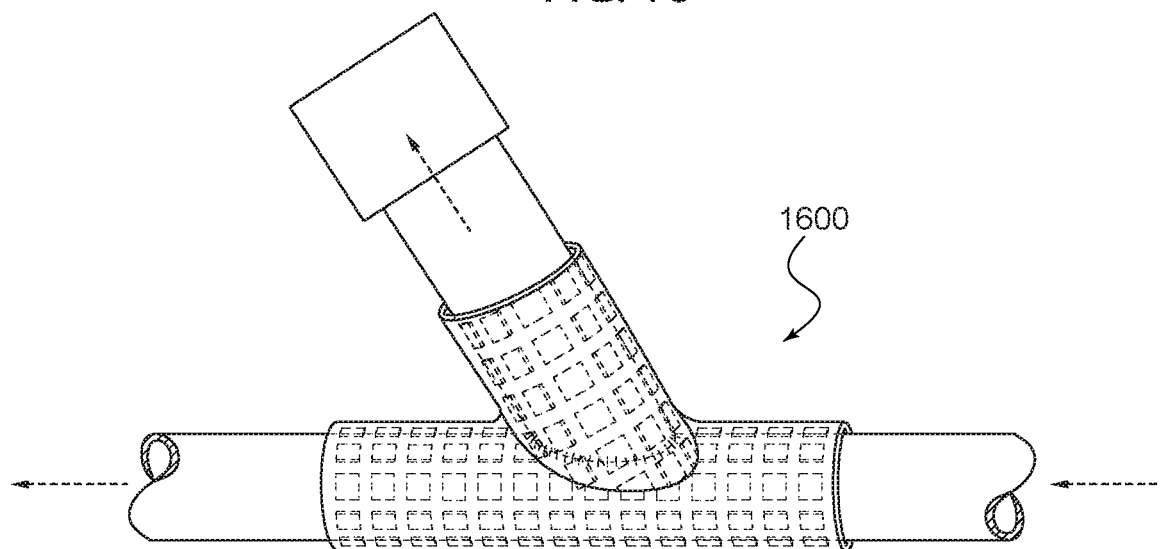
FIG. 16 illustrates a magnetized graft collar configured to wrap around a portion of an arterial anastomosis or a venous anastomosis, in accordance with practice of exemplary embodiments of the present invention.

For example, and without limiting the scope of the present invention, FIG. 16 illustrates a magnetized graft collar configured to wrap around a portion of an arterial anastomosis or a venous anastomosis, in accordance with practice of exemplary embodiments of the present invention. More specifically, FIG. 16 depicts magnetized graft collar (graft collar 1600) wrapped around a portion of an artery or vein, that is connected to a terminal end of a magnetic vascular access device in accordance with the present invention.

Figure 17:
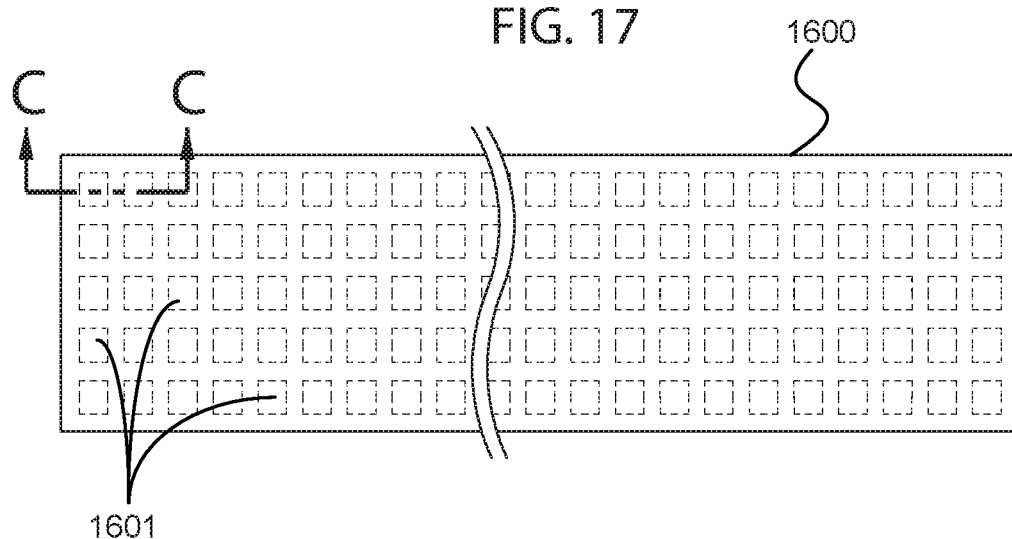
FIG. 17 illustrates a top view of a magnetized graft collar in accordance with practice of exemplary embodiments of the present invention.

FIG. 17 illustrates a top view of graft collar 1600, which is shown unraveled and laid out flat as it would be prior to application. From this view it may be appreciated that the magnetic graft collar 1600 may comprise of a mesh body including at least two layers of a flexible substrate 1602; and a plurality of magnetic crystals 1601 disposed between the at least two layers of the flexible substrate.

Figure 18:
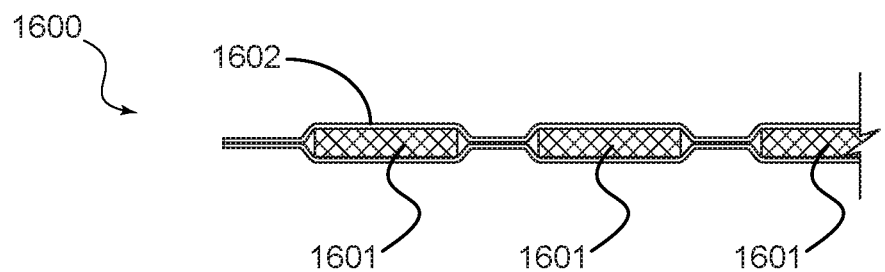
FIG. 18 illustrates a close-up cross-sectional view of a magnetized graft collar in accordance with practice of exemplary embodiments of the present invention.

FIG. 18 illustrates a close-up cross-sectional view of the magnetized graft collar 1600. From this view, it may be appreciated that in some exemplary embodiments, each of the magnetic crystals 1601 may be sandwiched between the two layers. In some exemplary embodiments, silver and or copper may be included with the magnetic crystals 1601— their anti-microbial properties may be desirable. Of course, a person of ordinary skill in the art will appreciate that other configurations may be possible without deviating from the scope of the present invention. In some exemplary embodiments, more than two layers or only a single substrate is used and a plurality of magnetic components (such as magnetic crystals) may be adhered to or otherwise securely fixed onto the substrate.

Accordingly, a magnetic vascular access system, in accordance with some exemplary embodiments of the present invention, may include: a magnetic vascular access device 101 having a tubular body 106 of biocompatible material including an arterial end 107 adapted for arterial anastomosis to a portion of an artery, and a venous end 108 adapted for venous anastomosis to a portion of a vein; a first housing 112 running through the tubular body, the first housing 112 adapted to house a flow tube 113 for guiding a blood flow between the arterial end and a venous end; a second housing 106a encapsulating the first housing 112 and forming a cavity 114 between the first housing 112 and the second housing 106a, the cavity 114 including a plurality of magnets 117 configured to generate a magnetic field applied to the blood flow guided through the flow tube 113; and at least one cannulation port 111 arranged on a surface of the tubular body 106, the cannulation port 111 configured for receiving needle punctures providing needle access to the first housing 112; and a magnetized graft collar 1600 configured to wrap around a portion of an arterial anastomosis or a venous anastomosis. As mentioned above, the magnetic graft collar 1600 may comprise of a mesh body 1602 including at least two layers of a flexible substrate; and a plurality of magnetic crystals 1601 disposed between the at least two layers of the flexible substrate.

The foregoing detailed description has set forth various embodiments of the devices and/or processes by the use of diagrams, flowcharts, and/or examples. Insofar as such diagrams, flowcharts, and/or examples contain one or more functions and/or operations, it will be understood by those within the art that each function and/or operation within such diagrams, flowcharts, or examples may be implemented, individually and/or collectively, by a wide range of hardware, software, firmware, or virtually any combination thereof.

Those skilled in the art will recognize that it is common within the art to describe devices and/or processes in the fashion set forth herein, and thereafter use engineering practices to integrate such described devices and/or processes into other similar systems. That is, at least a part of the devices and/or processes described herein may be integrated into a vascular access device system via a reasonable amount of experimentation.

The subject matter described herein sometimes illustrates different components contained within, or connected with, other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

A system and method for magnetizing a vascular access graft has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

What is claimed is:

1. A system, comprising:
   a magnetic vascular access device, comprising:
      a tubular body of biocompatible material including an arterial end adapted for arterial anastomosis to a portion of an artery, and a venous end adapted for venous anastomosis to a portion of a vein;
      a housing running through the tubular body and adapted to house a flow tube for guiding a blood flow between the arterial end and the venous end;
      a cavity formed within the housing and adapted to encapsulate the flow tube, the cavity including a plurality of magnets configured to apply a magnetic field to the blood flow guided through the flow tube; and
      at least one cannulation port arranged on a surface of the tubular body, the cannulation port configured for receiving needle punctures providing needle access to an interior of the flow tube; and
   a magnetized graft collar configured to wrap around a portion of an arterial anastomosis or a venous anastomosis, wherein the plurality of magnets of the magnetic vascular access device are configured in alternating or non-alternating polarities.

2. The system of claim 1, wherein the magnetic graft collar comprises:
   a mesh body including at least two layers of a flexible substrate; and
   a plurality of magnetic crystals disposed between the at least two layers of the flexible substrate.

3. The system of claim 1, wherein the magnetic graft collar further comprises silver and copper disposed between at least two layers of the flexible substrate.

4. The system of claim 1, wherein the plurality of magnets of the magnetic vascular access device are diametrically magnetized.

5. The system of claim 1, wherein the plurality of magnets of the magnetic vascular access device are axially magnetized.

6. The system of claim 1, wherein the tubular body of the magnetic vascular access device further comprises:
   at least one cannulation port arranged on a surface of the tubular body, the cannulation port configured for receiving needle punctures providing needle access to an interior of the flow tube.

7. The system of claim 1, wherein the tubular body of the magnetic vascular access device forms a U-shape between the arterial end and the venous end.

8. The system of claim 1, wherein the tubular body of the magnetic vascular access device further comprises:
   at least one cannulation port arranged on a surface of the tubular body, the cannulation port configured for receiving needle punctures providing needle access to an interior of the flow tube.

9. A system, comprising:
   a magnetized graft collar configured to wrap around a portion of an arterial anastomosis or a venous anastomosis, the magnetized graft collar comprising:
      a mesh body including at least two layers of a flexible substrate; and
      a plurality of magnetic crystals disposed between the at least two layers of the flexible substrate; and
   a magnetic vascular access device, comprising:
      a tubular body of biocompatible material including an arterial end adapted for arterial anastomosis to a portion of an artery, and a venous end adapted for venous anastomosis to a portion of a vein;
      a housing running through the tubular body and adapted to house a flow tube for guiding a blood flow between the arterial end and the venous end; and
      a cavity formed within the housing and adapted to encapsulate the flow tube, the cavity including a magnetic element configured to apply a magnetic field to the blood flow guided through the flow tube.

10. The system of claim 9, wherein the magnetic graft collar further comprises silver and copper disposed between the at least two layers of the flexible substrate.

11. The system of claim 10, wherein the magnetic element comprises of a plurality of magnets.

12. The system of claim 11, wherein the plurality of magnets of the magnetic vascular access device are configured in alternating polarities.

13. The system of claim 11, wherein the plurality of magnets of the magnetic vascular access device are configured in non-alternating polarities.

14. The system of claim 11, wherein the plurality of magnets of the magnetic vascular access device are diametrically magnetized.

15. The system of claim 11, wherein the plurality of magnets of the magnetic vascular access device are axially magnetized.

16. The system of claim 10, wherein the magnetic element comprises of a circuitry configured to generate a magnetic field.

17. The system of claim 10, wherein the tubular body of the magnetic vascular access device is configured to spiral between the arterial end and the venous end to allow adjustment of a length and a width of the tubular body.

18. The system of claim 10, wherein the tubular body of the magnetic vascular access device forms a U-shape between the arterial end and the venous end.

* * * * *